US007086409B2

(12) United States Patent
Robinson

(10) Patent No.: US 7,086,409 B2
(45) Date of Patent: Aug. 8, 2006

(54) FLUID CONTROL ISLAND

(75) Inventor: Allan R. Robinson, Minneapolis, MN (US)

(73) Assignee: Promethean Medical Technologies, Inc., St. Paul, MN (US)

( * ) Notice: Subject to any disclaimer, the term of this patent is extended or adjusted under 35 U.S.C. 154(b) by 0 days.

(21) Appl. No.: 10/892,534

(22) Filed: Jul. 15, 2004

(65) Prior Publication Data

US 2005/0133092 A1    Jun. 23, 2005

Related U.S. Application Data

(63) Continuation of application No. PCT/US03/01435, filed on Jan. 16, 2003, which is a continuation-in-part of application No. 10/053,141, filed on Jan. 16, 2002, now Pat. No. 6,637,453, which is a continuation-in-part of application No. 09/562,064, filed on May 1, 2000, now Pat. No. 6,938,639, which is a continuation-in-part of application No. 09/020,708, filed on Feb. 9, 1998, now Pat. No. 6,568,419.

(51) Int. Cl.
*E03B 1/00* (2006.01)
(52) U.S. Cl. ............ 137/1; 137/312; 137/561 R; 128/849; 128/855; 604/356; 220/571; 141/86; 141/88
(58) Field of Classification Search ............ 137/312, 137/1, 561 R; 128/849, 855; 604/356; 220/571; 141/86, 88
See application file for complete search history.

(56) References Cited

U.S. PATENT DOCUMENTS

| | | | |
|---|---|---|---|
| 2,851,311 A | 9/1958 | Gibbs | |
| 3,494,356 A | 2/1970 | Melges | |
| 3,589,365 A | 6/1971 | Sejman | |
| 4,243,214 A | 1/1981 | Larooka | |
| 4,295,235 A | 10/1981 | Deitz | |
| 4,598,458 A | 7/1986 | McAllester | |
| 4,635,913 A | 1/1987 | Rothman | |
| 4,679,590 A | 7/1987 | Hergenroeder | |
| 4,718,653 A | 1/1988 | Rothman | |
| 4,729,404 A | 3/1988 | Hergenroeder | |
| 4,811,937 A | 3/1989 | Rothman | |
| 4,870,710 A | 10/1989 | Hartmann | |
| 4,890,628 A | 1/1990 | Jackson | |
| 4,974,604 A | 12/1990 | Morris | |
| 5,002,069 A | 3/1991 | Thompson | |
| 5,078,705 A | 1/1992 | Edwards et al. | |
| 5,189,743 A | 3/1993 | Difloe | |
| 5,199,457 A | 4/1993 | Miller | |
| 5,287,860 A | 2/1994 | Owens | |
| 5,349,965 A * | 9/1994 | McCarver | ............ 128/846 |
| 5,452,739 A | 9/1995 | Mustee et al. | |
| 5,492,158 A | 2/1996 | Haag | |

(Continued)

*Primary Examiner*—Kevin Lee
(74) *Attorney, Agent, or Firm*—Schwegman, Lundberg, Woessner & Kluth, P.A.

(57) ABSTRACT

A fluid collection system having an island with a central collection vessel with a splash pad filling the opening thereof and a fluid collecting surgical drape with fluid dams, and associated fluid removal ports for collecting fluids related to surgical procedures from the vicinity of a patient positioned on the drape on an operating room table.

42 Claims, 8 Drawing Sheets

U.S. PATENT DOCUMENTS

| | | |
|---|---|---|
| 5,494,050 A | 2/1996 | Reyes |
| 5,503,163 A | 4/1996 | Boyd |
| 5,547,312 A | 8/1996 | Schmitz, Jr. |
| 5,675,854 A | 10/1997 | Zibelin |
| 5,709,221 A | 1/1998 | Vancaillie et al. |
| 5,738,139 A | 4/1998 | DeChard |
| 5,775,869 A | 7/1998 | Bishop |
| 6,269,815 B1 * | 8/2001 | Jascomb .................... 128/849 |
| 6,314,958 B1 * | 11/2001 | Harroll et al. ............. 128/849 |
| 6,568,419 B1 | 5/2003 | Robinson et al. |
| 6,938,639 B1 | 9/2005 | Robinson |

* cited by examiner

FLUID CONTROL ISLAND

REFERENCE TO RELATED APPLICATIONS

This application is a continuation under 35 USC 111(a) of International Application No. PCT/US03/01435 filed Jan. 16, 2003 and published in English as WO 03/061505 A1 on Jul. 31, 2003, which is a continuation-in-part U.S. application Ser. No. 10/053,141 filed Jan. 16, 2002 (U.S. Pat. No. 6,637,453), which is a continuation-in-part of U.S. application Ser. No. 09/562,064 filed May 1, 2000, which is a continuation-in-part of U.S. application Ser. No. 09/020,708, filed Feb. 9, 1998 (U.S. Pat. No. 6,568,419).

TECHNICAL FIELD

The present invention relates to methods and apparatus for control of fluids in work areas. More specifically, the invention relates to methods and disposable apparatus for collecting fluids emanating from a work area. In particular, the present invention provides apparatus and methods for collecting and quantifying the amount of infused and bodily fluids released during surgical procedures, for example during hysteroscopy and urology procedures.

BACKGROUND

A problem affecting the health and safety of a variety of workers is that of providing a safe, non-slippery, dry area upon which the workers can stand. Hospital operating room personnel are routinely required to stand and work in conditions in which the floor is inundated with several liters of distension media, blood, bodily fluids, and other liquids during a single procedure. The abundance of fluids released during surgery is due in part to refinements to diagnostic and surgical equipment, especially the improvements to endoscopic equipment and the widespread implementation of improved surgical techniques, especially the laparoscopic surgical techniques made possible by improved laparoscopy and other endoscopy tools during recent years.

Fluids dispersed onto operating room tables and floors are a considerable inconvenience to workers, increase the likelihood of contamination, and elevate the potential for spread of infectious disease.

Hysteroscopic, urologic, and some other surgical patients are often infused with a fluid distension medium. If a non-electrolytic distension medium enters the circulatory system, it can cause blood dilution and lowered ionic strength. Swelling can result as tissue takes up water to restore the correct blood osmolarity. A patient can suffer serious, or even fatal, complications if too much distension media is absorbed.

The amount of distension media that a patient can absorb without intolerably dangerous adverse effects is related in non-intuitive ways to various individual physical, chemical, and other factors. The preoperative nurse will estimate the volume of distension media that each patient is reasonably expected to absorb without complications by factoring the patient's age, weight, fitness, hormonal balance, the formulation of the distension media, the procedure being performed, and a host of other variables before the patient arrives in the operating room. Unfortunately, the full utility of that estimate can be realized only if the amount of fluid actually retained by the patient can be timely determined with sufficient accuracy while the procedure is being performed.

Based on these factors, it is easy to understand that surgeons, hospitals, and their patients would be greatly assisted by more accurate knowledge of the amount of distending medium retained by surgical patients.

To that end, surgeons often request the operating room personnel to report the amount of fluid that has been introduced into and received from the patient. Fluid limits are normally fixed between 500 ml and 1,500 ml., and surgery time is frequently limited to one hour. Unfortunately, it is difficult to reliably measure the volume of distension media received from the patient using traditional methods and equipment. Likewise, it is difficult to measure the volume of fluid infused with traditional methods and equipment.

In the effort to more accurately evaluate the amount of distension media returned by the patient, surgical drapes may be arranged to direct the returned fluid to buckets positioned on the floor. It can be necessary to halt the surgery while the unsterile contents of the buckets are measured. But, as can be seen from studying Table 1, the estimation errors for the amounts of fluid on the operating table and on the floor can be so large that there is little value in knowing the volume of fluid accumulated in the kick buckets.

What is needed is a practical way to collect fluids returned from a patient during hysteroscopic surgical procedures.

Also needed is a way to measure the volume of fluids returned from a patient during hysteroscopic surgery.

Another need is a practical way to collect fluids returned from a patient during urological surgical procedures.

An additional need is for a way to measure the volume of fluids returned from a patient during urological surgery.

A further need is for a way to collect and contain fluids discharged by a patient during childbirth.

Another need is for a way to collect and remove fluids received from a patient during orthopedic surgeries.

Another need is for a disposable surgical and diagnostic fluid control system having an integral drape.

Also needed is a fluid control system having pre-formed resilient dams to route fluids toward a collection point.

Yet another need is for a fluid control system having integral channels for routing suction tubing.

Yet another need is for apparatus making it possible to quickly determine the difference between the amount of distension media that has been infused into the patient and the amount of distension media that has been returned from the patient.

Embodiments of the present disclosure meet these needs, and more, by solving the long-recognized problem of containing and removing fluids received from surgery patients so that the volumes of the fluids can be measured and liquid dispersal throughout the working area can be minimized.

DETAILED DESCRIPTION

The construction of fluid control islands for diagnostic and surgical procedures may be understood viewing the accompanying FIGS. 1 through FIG. 11.

Figure 1:
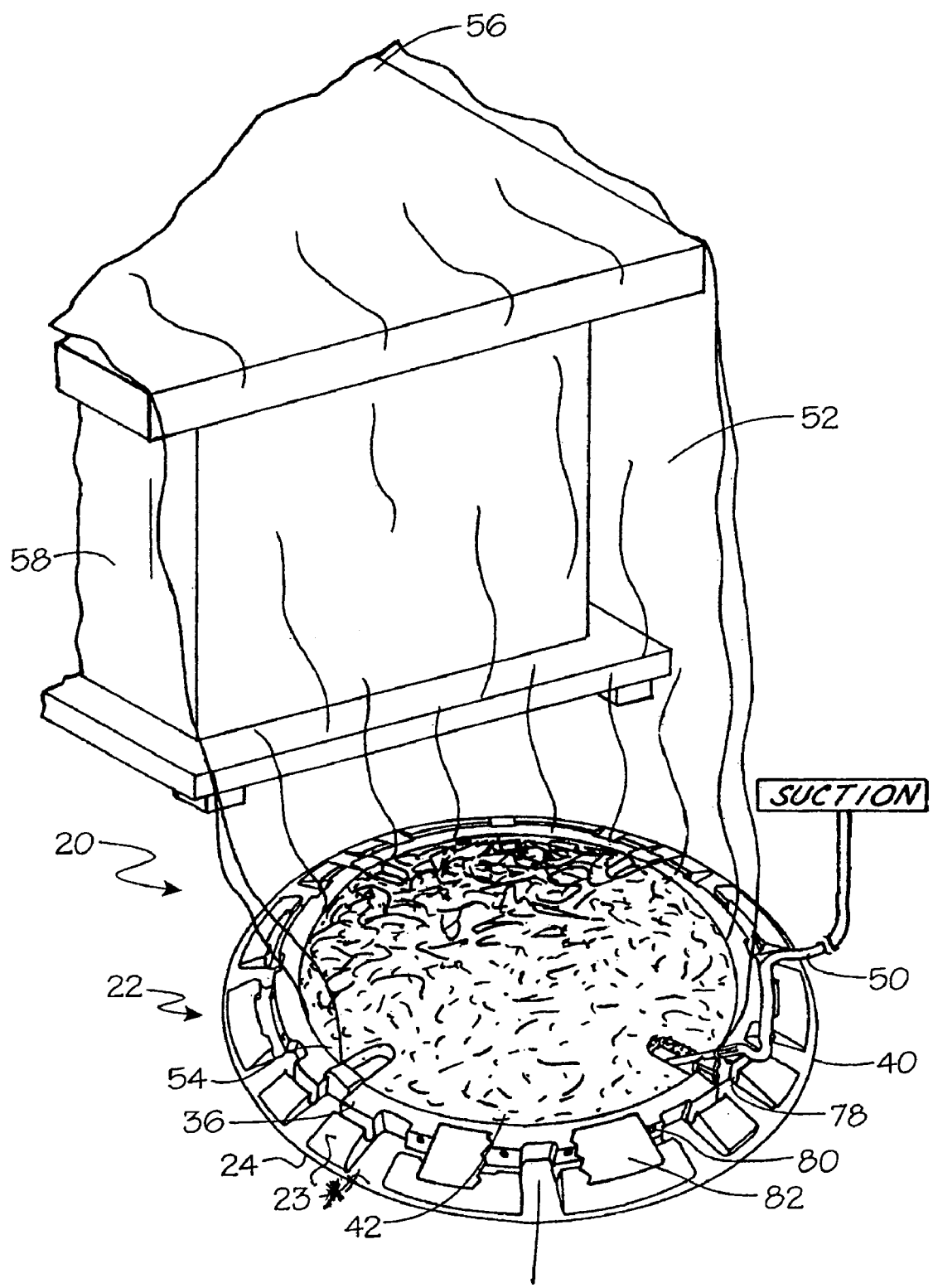
FIG. 1 is a perspective view showing a surgical fluid collection system with a surgical drape and a fluid removal means.

FIG. 1 shows, in perspective, an embodiment of a surgical fluid collection island 20 positioned for typical use on an operating room floor. In one embodiment the island is placed between a surgeon and an operating table for collecting and retaining various fluids emanating from patients during surgical procedures.

The collection island 20 has a broad, shallow, impermeable vessel-forming base having a central region surrounded by a further region 25. The island 20 may be formed from a variety of materials suitable for being formed by stamping, injection molding, vacuum forming, rotary molding, blow molding, and other techniques to produce a generally horizontal tray part. The base may be made of any impermeable material, for example recycled plastic soda containers. The base may also be made of impermeable sheet foam, metal foil, coated paper, or other materials. Sheet stock made from recycled beverage containers is widely available in a thickness between about 25 and 30 mil which can be readily vacuum-formed to produce an island 20 having good shape-retention characteristics.

Further region 25 has a peripheral outer edge 40, which is generally flush with a suitable support surface, such as an operating room floor. At least some portions of the upper surface 23 of further region 25 slope gently upwardly from the peripheral edge thereof to a summit 27 which is at the top of a substantially vertical peripheral wall 32 which marks a boundary between the central region and further region 25 and also defines the peripheral wall for the fluid collecting vessel in the central region.

Figure 4:
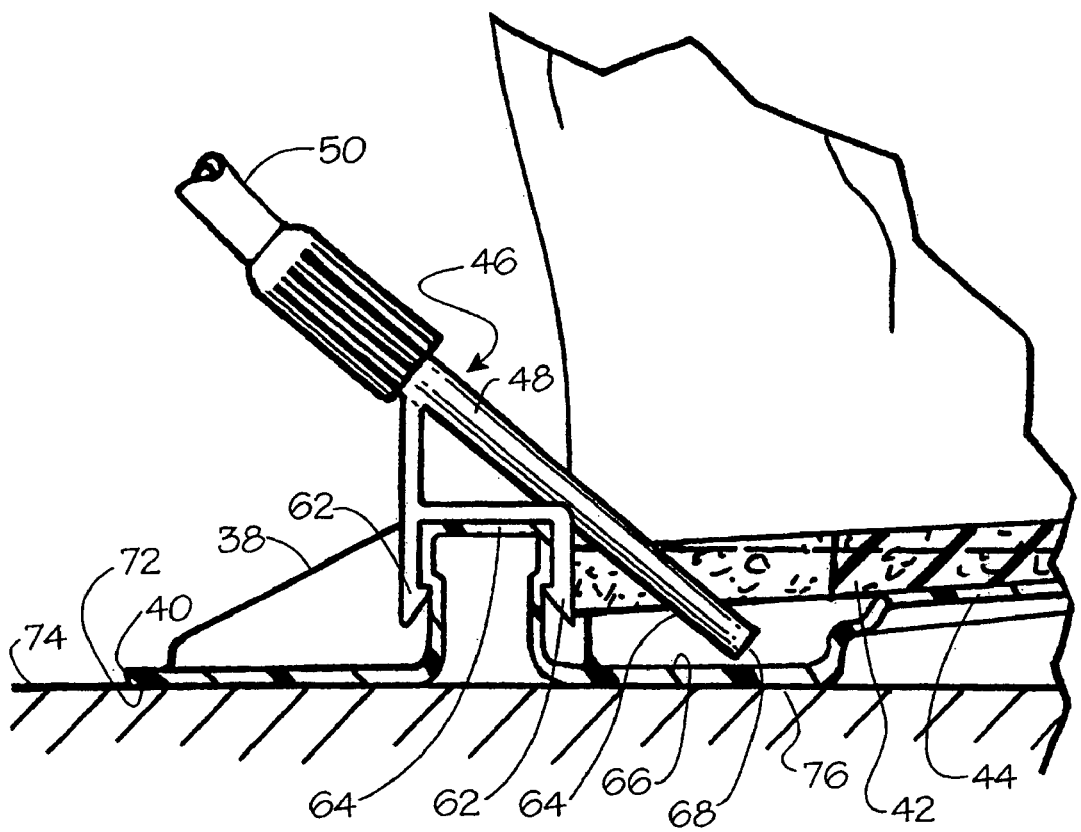
FIG. 4 is a sectional detail of the system showing the suction port and connection in greater detail.

As shown in FIG. 1, an embodiment of the island 20 is formed with sloping grooves or channels 28 on the vessel floor that route fluid received in the fluid contacting portion or wetted portion of the island 20 to a fluid collection or evacuation well 66 as shown best in FIG. 4.

An embodiment of the island also includes a suitable fluid removal fitting or other means for coupling a fluid conduit to for connecting suction proximate the evacuation wells.

An embodiment of the island also includes a splash-arresting pad 42 that covers the wetted area 34 of the island 20. The splash control pad 42 may be made of woven or non-woven textile, a macro-porous open-celled foam or other material, preferably a material that does not retain or absorb fluids.

It is desirable to have central portion of island 20 constructed with the floor thereof having a low modified conical shape where the central wetted area 34 of the central portion is covered by splash pad 42 and a lower end 54 of a surgical drape 52 is affixed to the peripheral wall of the vessel in the central portion. In one embodiment, drape 52 is affixed to about three fourths of the total circumference of the vessel in the central portion of island 20.

The floor of the vessel in the central region is generally tapered downwardly from a central apex region 26 to the base of peripheral wall 32 with a radial array of ribs 44 that support the splash pad 42 above hollowed-out downwardly sloping channels 28 which lie between the ribs 44.

In one embodiment the island 20 may have a radius of six inches for the central, wetted region, and the further peripheral skirt, region 25 having annular dimension of 2½ inches, the overall island diameter will be seventeen inches. In one embodiment the island may have may have the apex region at the center of the central region extend about ¾ inch above the floor or other equivalent supporting surface.

In one embodiment, a peripheral groove or channel 30 is formed at the circumference (or periphery) of the fluid capturing wetted area 34, at the base of peripheral wall 32, for enhanced fluid flow communication between the fluid evacuation wells 66 and a suction fitting 46. In one embodiment, the suction fitting 46 may be affixed at any of several collection wells 76 so as to move it out of the way of the surgical personnel. If the floor happens to be slanted, fitting 46 may be attached to access the lowest of the collection wells 76.

The floor or other supporting surface supports the under-surface of the island including the undersurface portion of the bottom of the peripheral channel 30 and at the undersurface portion of the bottoms of the fluid evacuation wells 76 in addition to the peripheral outer edge of the skirt or further region 25. This configuration allows fluids to flow quickly by gravity through the splash-preventing pad, or mesh, 42 down sloping channels 28 to a relatively narrow peripheral channel 30 that has a low retained fluid volume and into the collection wells 76 from which it may be evacuated. Although fluids can be extracted from all of the evacuation wells 76, it is generally sufficient to evacuate the fluids from one well using vacuum suction where the fluids are then collected in vacuum canisters of any now known or later-developed type.

A tubing guide channel 78 formed in the skirt or further region 25 may provide suction tubing management. Walls of the tubing guide channel 78 may have protrusions or detents 80 to retain the tubing 50 after it has been placed into channel 78. An optional tubing retaining member 82 such as a retainer plate or flap may be formed of the same stock as the island 20, or from different material, and affixed to the further region 25 at one or more locations in any manner, for example, by sonic welding, adhesive, solvent welding, mechanical fasteners, or heat sealing, to keep the suction tubing 50 in the desired location. The tubing guide channel 78 may conveniently encircle the central region of island 20 to simplify assembly by removing any necessity for orientation of that element with others.

In one embodiment the distal portion 54 of a polyethylene surgical drape 52 may optionally be affixed to at least a portion of the inner wall 32 of island 20 so that fluids are reliably collected and conveyed to a fluid collection well for removal suction. Drape 52 may also be fitted with an optional tissue and debris collection pocket 84 having a liquid-permeable screen or mesh 85 inserted therein and a drain opening 86 to drain the pocket 84 below the screen 85.

In one embodiment additional integral resilient fluid containment elements may be formed in the proximal portion 56 of drape 52. That portion of the drape 52 which is to be positioned between the patient and the top of the operating table is provided with fluid containment dams by sealing portions of the sides of the drape 52 and its proximal end 54 over and around a somewhat resilient member 90 such as urethane foam rod or strip, macro-porous open-celled foam, non-woven mesh, sponge, or innumerable other materials. Resilient member 90 elevates the proximal end 54 of the drape 52 drape material slightly above the table and prevents fluids from flowing under the patient or over the side of the operating table. Use of the resilient member to form a fluid dam to retain fluid on the surface of drape 52 is particularly important for certain surgical procedures where the surface of the operating table is angled downwardly from the end of the table over which the drape 52 passes to perform procedures such as Trendelenburg procedures.

In some embodiments drape 52 may optionally be sterile or sterilizable or non-sterile.

Although island 20 is not intended to support a person, however, it should not be harmed if one either steps or stands on it. In one embodiment, a resilient foam support post may be affixed to the underside of the apex region 26 to prevent the cone pitch from inverting as the result of someone stepping on the island.

In one embodiment the fluid control island is small enough, with a diameter of approximately 17 inches, to fit between the feet of the surgeon and to also be readily relocated if desired. Although the island is depicted as round, it is to be understood that other shapes such as square, rectangular or elliptical will also work.

When the procedure is finished, suction may be disconnected, the drape removed from beneath the patient, and the drape, base and any tubing placed in a bag for proper disposal, usually by incineration. With proper suction, fluid residence time in the base is very low, and the latent volume retained in the splash pad, the drape, and the base is usually less than approximately 75 ml.

In one embodiment the splash control pad 42 may have a mesh thickness of about ¼" to ¾." The conical drainage slope causes the liquid to flow from the raised apex region 26 radially outwardly through sloping channels 28 toward the peripheral fluid channel 30 and the evacuation wells 66 where suction removes the fluid to containers.

Removal of fluid from the island 20 can be accomplished with either a vacuum source and fluid collection canisters or directly with a pump suitable for pumping the specific liquids collected. The fluid control island, with the mat 42 in place, can contain a substantial volume of fluid giving the system a surge capacity making it possible to use a relatively low rate of fluid removal with an inexpensive removal system, whether vacuum operated or pumped directly, yet still have sufficient capacity to collect and remove all the fluids collected during a procedure. In one embodiment, a base having a 17" diameter and a depth of approximately ¾" has sufficient fluid surge capacity to handle most vaginal birth cases without overload.

It is believed that embodiments of the system integrated with surgical drapes with the fluid collection island can reduce spillage of fluids on the operating room floor to enable gynecology and urology surgeons to use general operating rooms rather than being restricted to specially equipped operating rooms. Such an advantage gained through use of embodiments of the invention could make it possible for patients and physicians to obtain these surgical services at many additional hospitals and clinics.

By collecting substantially all of the fluid received from a patient during hysteroscopic and urology procedures, it is possible to know with previously unobtainable accuracy how much distension media is discharged from the patient. It is also necessary to determine the amount of fluid introduced to the patient to compute the retained volume. In a further development of the invention, the container (usually a 3 liter flexible plastic bag) of distension media, together with any pressurizing device for forcing the fluid out of the container, is suspended from a scale that allows surgical personnel to determine the difference between the initial weight and the weight at any subsequent time. Conversion of the weight difference is straightforward since the density of the distension media is known. The fluid received from the patient can be drawn into collection canisters by house vacuum where the volume can be conveniently measured directly using calibrated containers.

Alternatively, collected fluid can be weighed using any of a variety of techniques to establish the differential between the weight of the fluids supplied to the surgical site and the weight of the fluids recovered using an embodiment according to this disclosure in addition to those returned from any other source (such as hysteroscope bypass or flushing). The fluid collected by the fluid control island may also be pumped to the collection containers. It may also be possible to weigh the distension media supply and the returned fluids collected on the same scale to achieve an accurate measure of fluid remaining in the patient in real time. Another alternative method is to measure the amounts of fluid introduced into and received from the patient with mass flow meters and compute the difference electronically to inform the surgical team of the amount of fluid retained by the patient.

Figure 2:
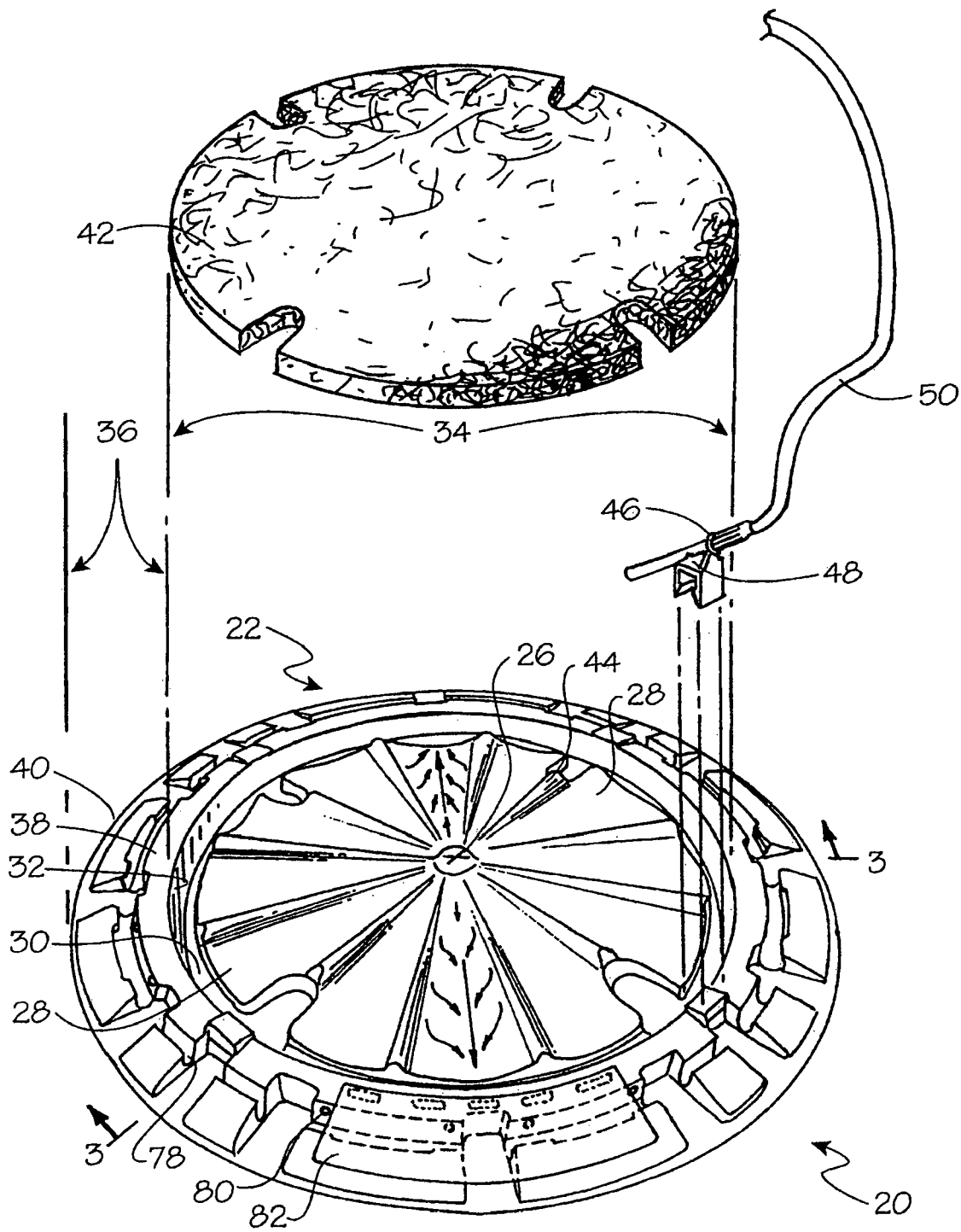
FIG. 2 is an exploded view of the system shown in FIG. 1.

As can be more clearly viewed in FIG. 2 the base 22 may be formed with a raised center 26 having sloping channels 28 sloping radially downwardly toward a lower peripheral channel 30 at the base of a generally vertical peripheral wall 32. The vertical peripheral wall 32 divides the island 20 into two regions because it is disposed between a fluid-contacting central portion 34 and a radially outwardly, or distally, disposed further or skirt region 36. A generally beveled upper skirt surface 38 extends between the top of the generally vertical peripheral wall 32 and a base edge 40 proximate the floor.

A generally non-absorbent splash pad 42 is disposed within the fluid-contacting central portion and supported by ribs 44 above the radial sloping channels 28 and extending proximal to the vertical peripheral wall 32, and means 46 for connecting 48 fluid-removing suction tubing 50 proximate the lower peripheral channel 30. In one embodiment, ribs 44 support the lower surface of pad 42 above the surface of the island 20 in channels 28 so that the material in pad 42 does nothing to restrict the flow of fluid through the channels 28 into peripheral channel 30 and collection wells 66.

The sloping channels 28 need not be radial, but could be downwardly sloping from the center toward the periphery of any shape. Retention of water is minimized by making the sloping channels 28 with conical, or scalloped, cross-sectional curvature (viewing in the direction of fluid flow) so that fluids impinging on the fluid-contacting central portion 34 is provided a fairly steep path down which to flow and by which droplets may converge to more rapidly flow to the lower peripheral channel 30 for removal.

Although in one embodiment a base 22 mating tubing connector 48 is illustrated, it is to be understood that other means for connecting 46 suction tubing 50 proximate the fluid channel 30 may be used equivalently. Examples of other potential means for coupling the suction tubing 50 to drain wells 66 and peripheral channel 30 include bulkhead connectors, adhesives, mechanical fasteners, and all other commercially available tubing connection devices. In some cases, it may be possible to insert suction tubing 50 directly into the peripheral fluid channel 30 below the splash pad 42.

Figure 6:
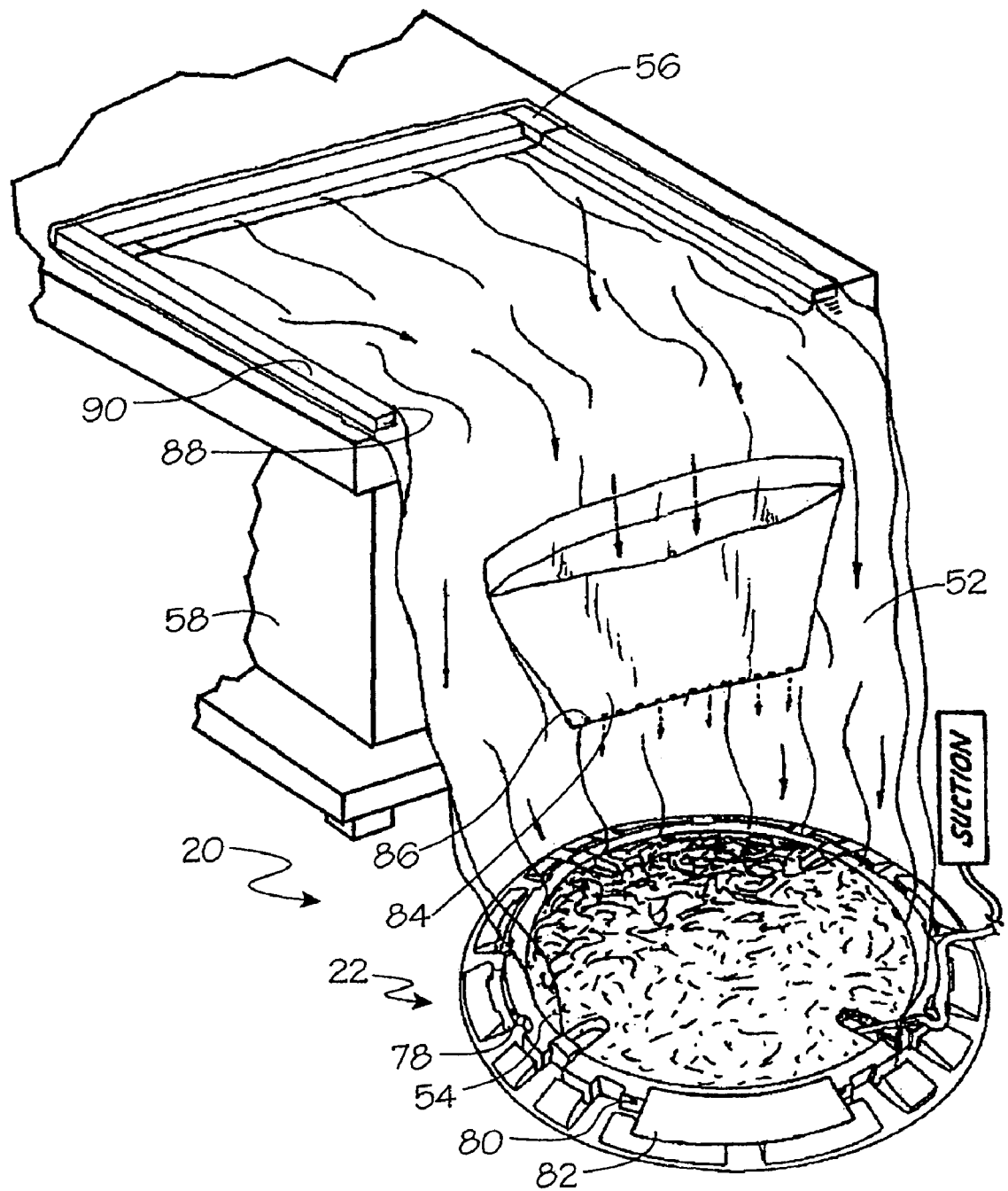
FIG. 6 is a perspective view of a further embodiment of the system depicting resilient dams formed integrally with the drape and a optional tissue and debris collection pouch with drain.
Figure 7:
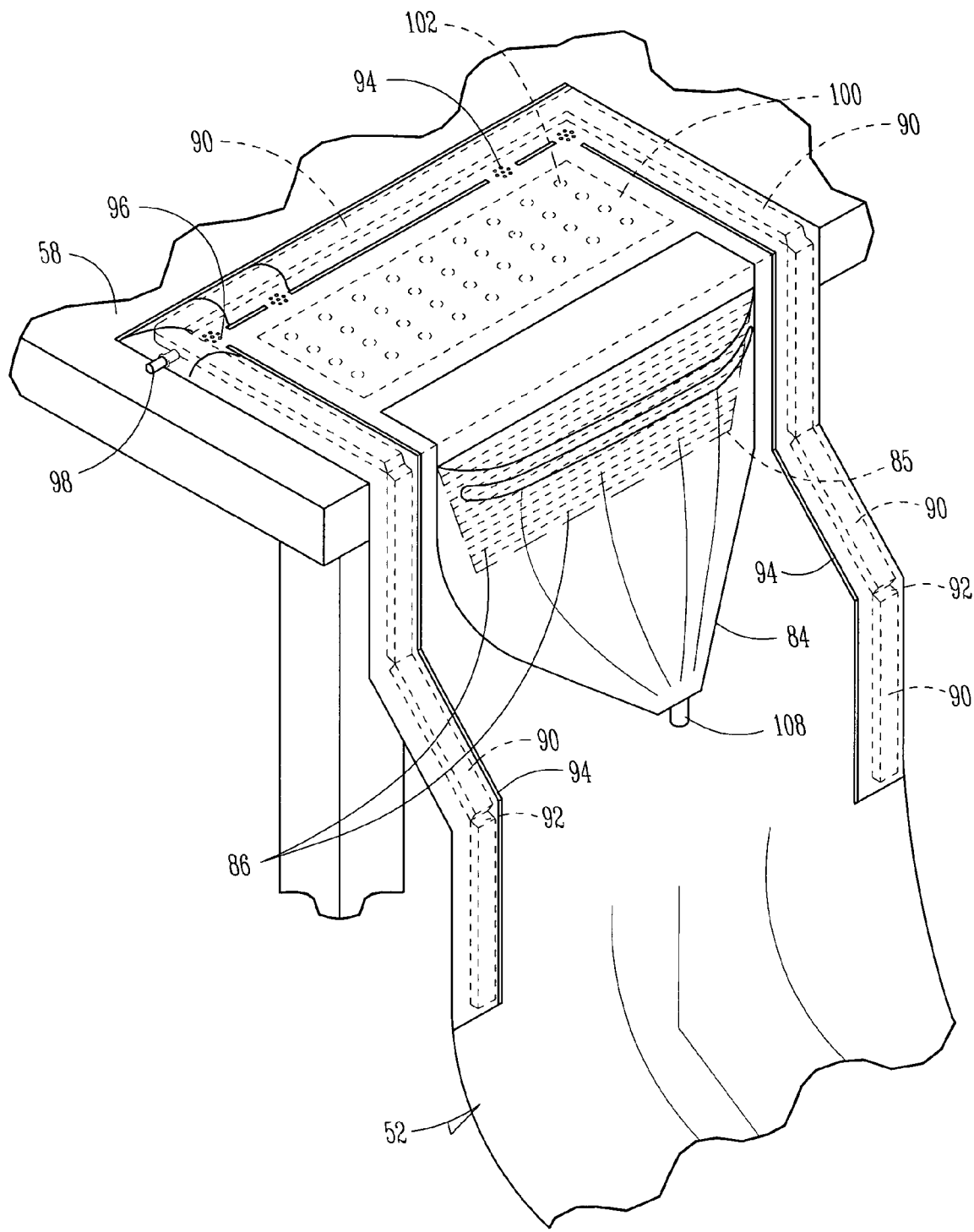
FIG. 7 is a perspective view of another embodiment of the surgical drape portions of the fluid collection system.

In one embodiment an elongated drape 52 lower end 54 is affixed to the base 22 proximate the peripheral wall and an elongated drape upper end 56, shown in FIGS. 1, 6 and 7 may be disposed upon an operating table 58 for fluid communication between a patient and the base 22.

Figure 3:
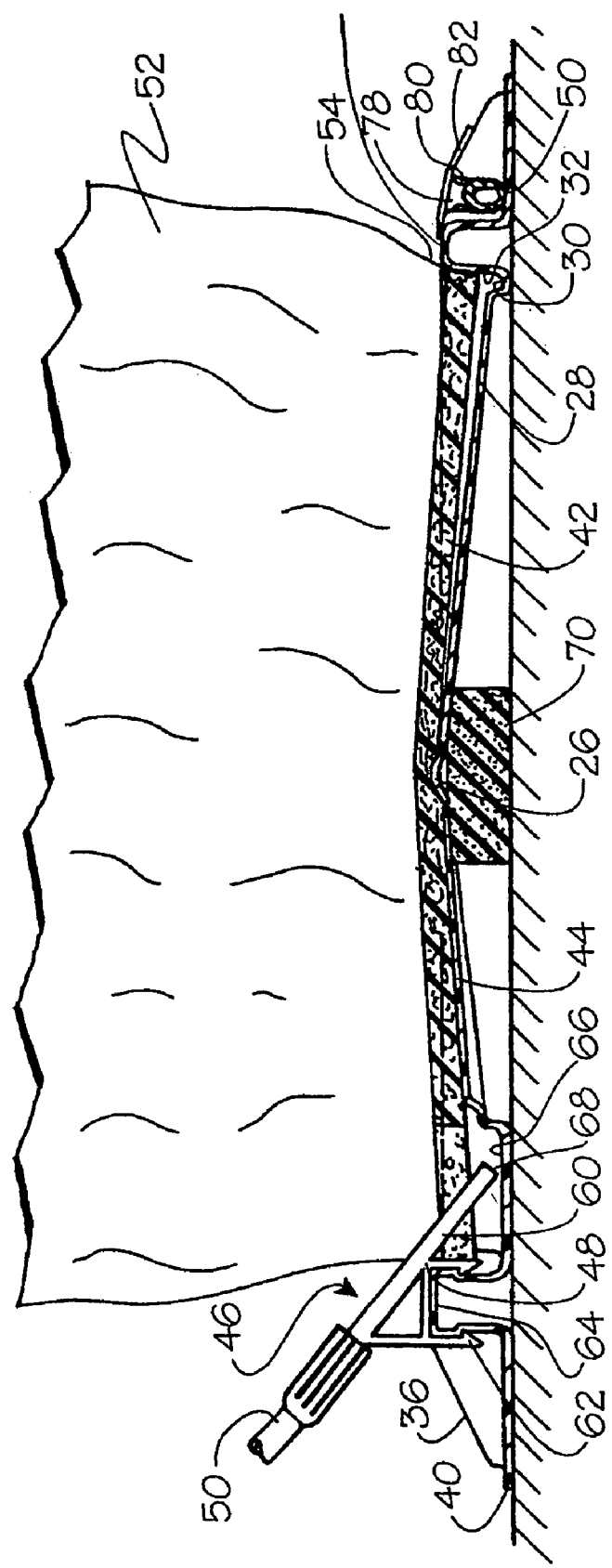
FIG. 3 shows two radial sections of the system of FIG. 2 taken at 3—3.

Viewing FIG. 3 shows two radial sections of the disposable surgical and diagnostic fluid control island 20 of FIG. 2 taken at 3—3. The sectional view illustrates one embodiment of a means for coupling suction tubing 50 to the island may be any convenient fitting but is preferably an angled suction tubing connector 48 having a tubular portion 60 and an integrally molded resilient catch 62 in at least one location that is matingly receivable on a land 64 formed into the upper edge of the skirt 36 at a plurality of locations. The tubular portion of the suction tubing connector can extend into fluid evacuation wells 66 that are formed to receive the suction tubing connector 48 with the inlet 68 proximate the lowermost portion of the wetted area of the base.

Although the fluid evacuation wells 66 may be provided in any convenient number, four are illustrated in the embodiment shown but only one suction connector 48 is illustrated and used. A peripheral fluid channel 30 receives fluids that run from any point within the peripheral wall 32 and conveys those fluids to the evacuation wells 66. Suction at one evacuation well 66 removes all fluid with the exception of a residual amount that is typically less than 75 ml for the complete apparatus, including an attached drape 52.

The raised center portion 26 of island 20 may be supported by a post 70 of solid or resilient material to support the apex region 26 to prevent crushing of and accidental inversion of the slope of the channels 28 in the event that the fluid control island is stepped upon or run over by a wheel of an instrument cart.

FIG. 4 shows the suction tubing connector 48 in greater detail mated on a land 64 with the bottom peripheral surface 72 adjacent the distal edge 40 of the base 22 in contact with the floor 74. The bottom surface 76 of the evacuation wells 66 may also contact the floor 74.

Figure 5:
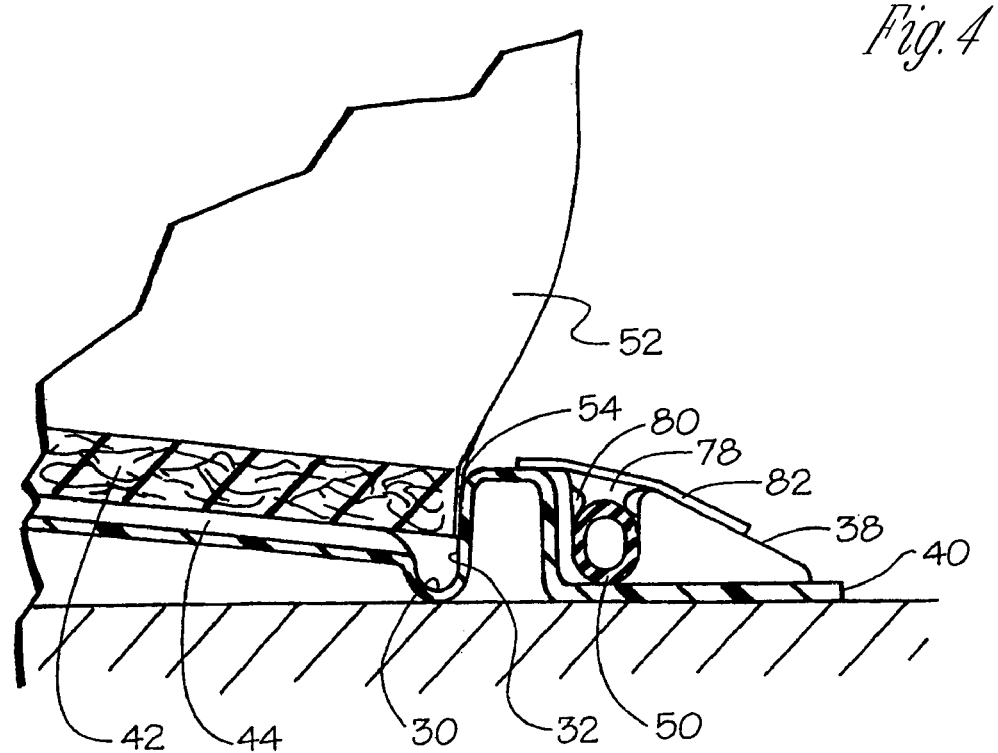
FIG. 5 is a sectional detail of the system showing the suction tubing installed in the tubing guide channel.

FIG. 5 shows a detail of the peripheral wall 32 and the peripheral channel 30 for fluid evacuation. The drape 52 distal end 54 is attached to the base 22 conveniently at the peripheral wall 32 by adhesive, heat seal, sonic welding, or other suitable means, depending upon the properties of the materials from which the components are made. The splash pad 42 extends to proximity with the drape lower end 54 and may be affixed to the center apex 26 and or ribs 44 by any convenient method. In some instances, anti-skid materials may be applied to the bottom surface 72 of island 20.

In one embodiment a generally peripheral suction tubing guide channel 78 is set into or formed in the upper skirt surface 38 of further skirt region 25, interposed between the peripheral wall 32 and the distal edge 40. In one embodiment the tubing guide channel 78 may extend circumferentially entirely around the island 20. In another embodiment it only extends part of the way. In another embodiment other structures are to the island to restrain suction tubing 50 from detaching from island 20.

In one embodiment tubing guide channel 78 may be equipped with protrusions, nibs or detents 80 for restraining the suction tubing 50 within the channel. In another embodiment it is also possible to form one or more generally planar tubing retainer members 82 resiliently disposed over the suction tubing guide channel 78. Fitting such a flap, hinge, cover, or other structure over the suction tubing guide channel 78 to confine the tubing 50 in the channel can keep the work area neater while preventing accidental disconnection of suction from island 20.

In one embodiment where the island 20 is made of a resilient material, it can be a simple matter to sonic weld a plate 82 of the same material over the channel 78 so that the suction tubing 50 may be easily placed into the channel 78 and remain there until intentionally removed.

FIG. 6 illustrates another embodiment of the fluid collection system where island 20 includes a surgical drape 52. In one embodiment, the drape may be pre-attached to the fluid control island. In another embodiment the drape 52 may include a preapplied adhesive strip at the lower margin thereof for engaging the peripheral wall 32. In one embodiment that drape may include a tissue and debris capturing strainer pocket 84 with a drain 86 for the convenient collection of tissue specimens that might require laboratory analysis. In one embodiment it may desirable to form a strainer pocket 84 integrally with the drape 52. It will be preferable in some cases to apply the pocket 84 after the patient is in position. The edges 88 of the upper end of the drape 56 that contacts the patient may be fitted with a resilient member 90 such as foam either on the table-contacting side of the drape or inside a folded-over edge 88 segment.

The resilient member 90 can raise the drape sufficiently to form a dam to prevent fluid from dispersing beneath the patient or along the patient's sides toward the head of the patient. Some surgical positions elevate the patient's buttocks during surgery. That can cause fluids that impinge on the operating table to flow away from the fluid collection island. In those cases, especially, it can be helpful to take the additional step of fitting resilient fluid dispersal blocking members 90 between the patient contacting surface of the drape 52 and the operating table 58.

Figure 11:
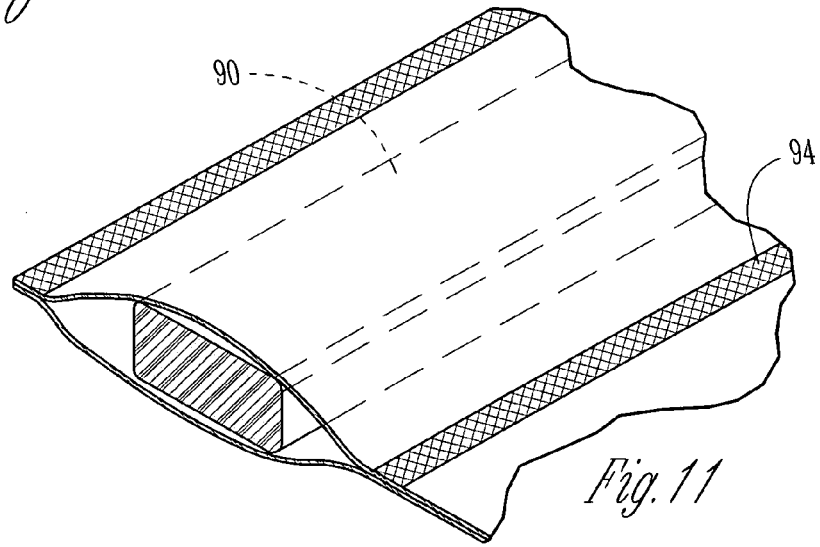
FIG. 11 is a perspective sectional detailed view taken along section lines 11–11' of FIG. 9 showing the enclosure of the resilient dam strip by the sheet material of the surgical drape of the system shown in FIG. 7.

FIG. 7 shows another embodiment of a fluid collecting system. In that embodiment resilient fluid blocking member 90 is cut with die cut notches 92 to facilitate unfolding of the drape 52 into the opened position shown in FIG. 7 from the folded configuration shown in FIG. 8. In one embodiment fluid blocking member 90 is cut into individual segments to facilitate folding rather than having 45° die cuts to form right angle notches 92 which removed from the resilient member 90 without cutting it into separate pieces. FIGS. 9 and 11 are detail views showing the welds 94 between sheets of drape material to secure blocking members 90 in their proper position at the edges of the surgical drape. In one embodiment, the top and bottom sheets are separate and bonded to secure the resilient member longitudinally, on both sides of the member. In another embodiment, a single sheet of doublewide material is folded over so that no long bond is required along that edge.

Figure 8:
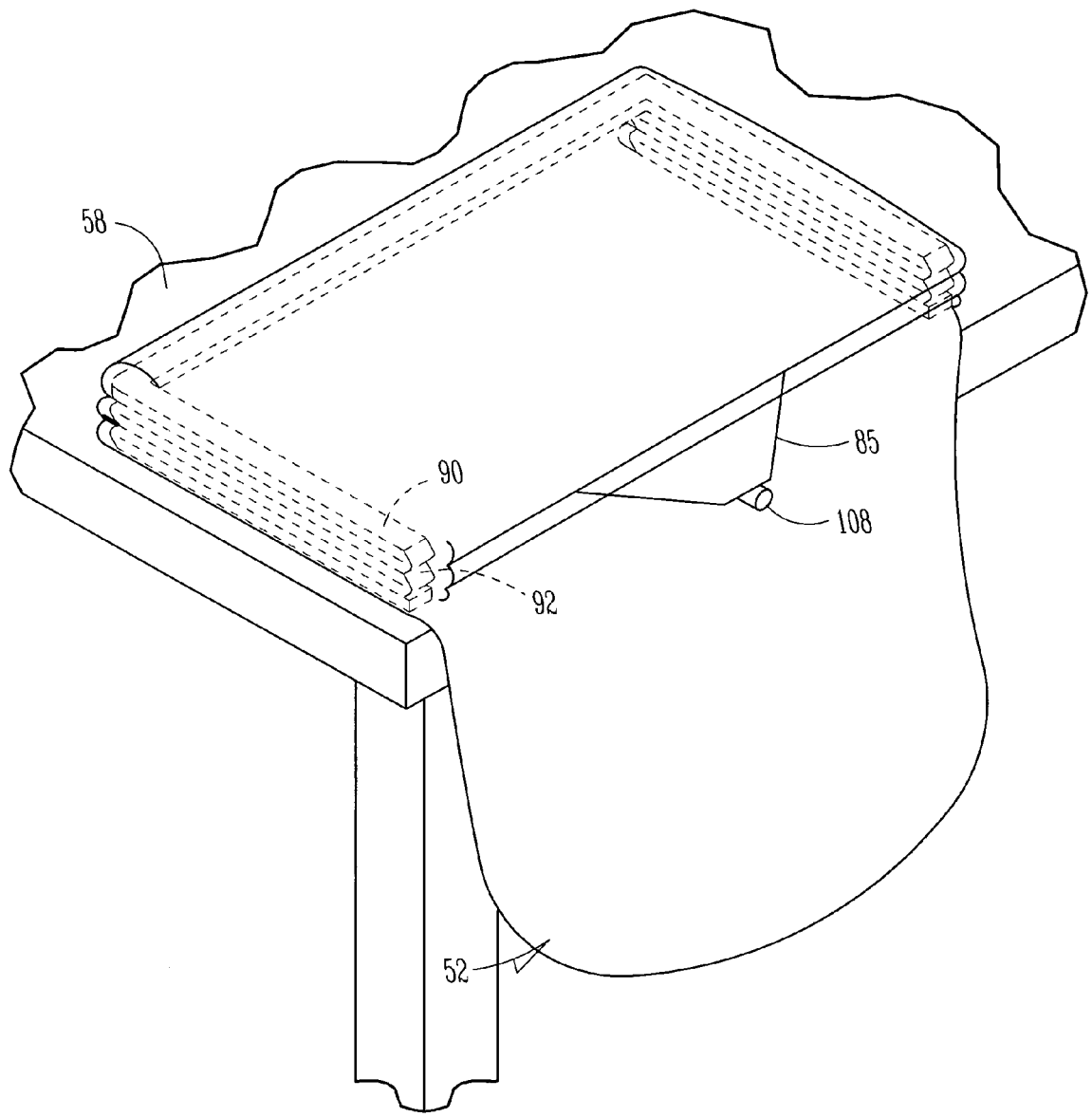
FIG. 8 is a perspective view of the surgical drape of the system shown in FIG. 7 with the end of the drape that is to be disposed upon the operating table shown in a folded configuration, ready for disposition and use.
Figure 9:
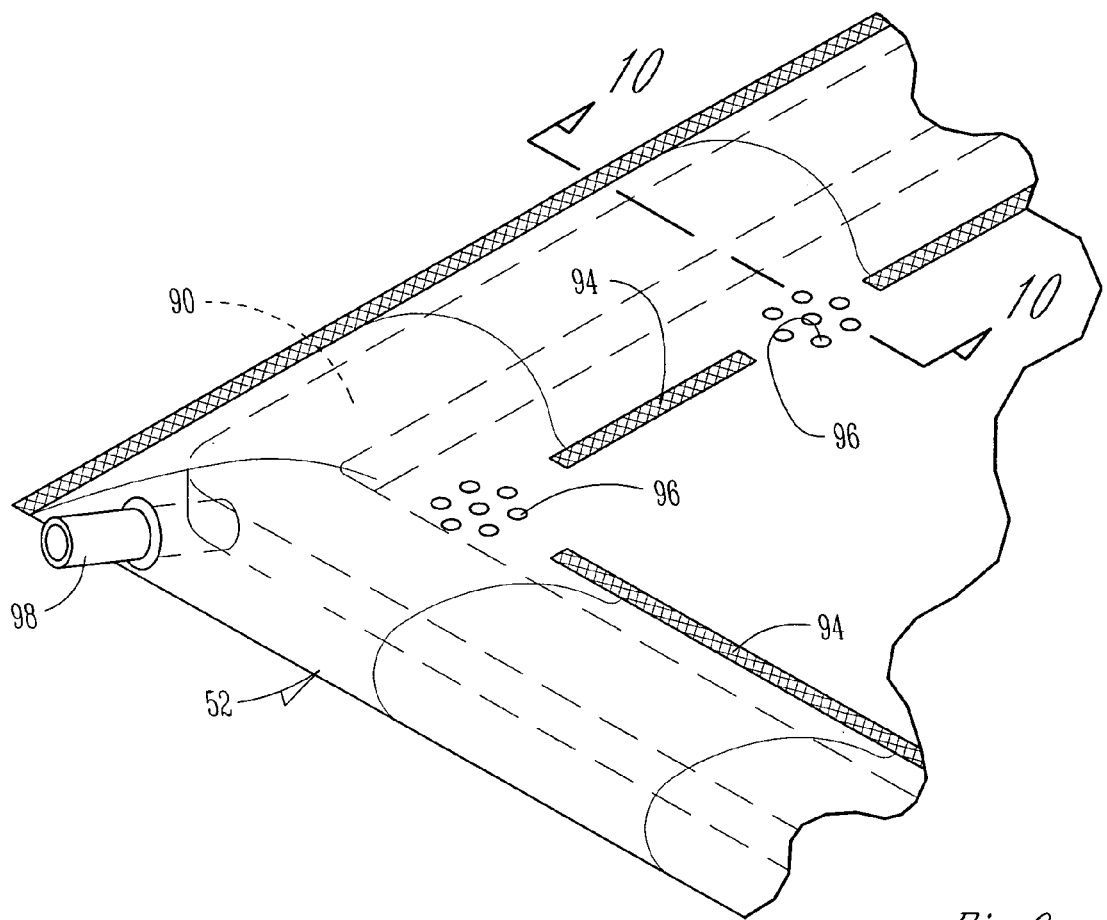
FIG. 9 is a detail perspective view of the a corner of the proximal end of the surgical drape of the system shown in FIG. 7.
Figure 10:
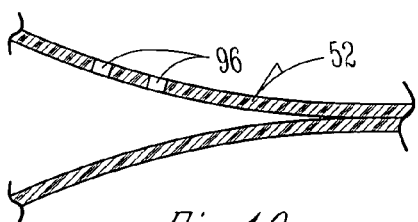
FIG. 10 is a perspective sectional detailed view taken along section lines 10–10' of FIG. 9 showing the provision of drain holes in the upper surface of the two layer surgical drape of the system shown in FIG. 7.

In some applications drape 52, made from PVC sheeting is placed on the edge of the operating table folded as shown in FIG. 8, the patient is positioned on the table and then the drape is unfolded to the position shown in FIG. 7 as the patient is lifted to provide clearance under to permit positioning of the drape.

In one embodiment, the top sheet of material in drape 52 has a plurality of apertures 96 there through, adjacent the fluid dam provided by resilient member 90. Resilient member 90 is a lightweight urethane foam between approximately 3/8" to 1/2" thick. Apertures 96 permit fluid moving away from the edge of the table toward the head of the patient to be captured in a chamber between the sheets of the drape and then evacuated from a fluid port 98.

In one embodiment a pad 100 is also placed between the sheets of the drape 52 to maintain a fluid collecting chamber even while the patient is lying on the drape. In one embodiment, pad 100 is a polyester or MYLAR macro porous support mesh to permit fluid entering the chamber to freely migrate toward fluid port 98. In one embodiment there are a plurality of apertures 102 penetrating through mesh 100 to reduce fluid retention in the mesh while allowing fluid to flow through the collecting chamber in the drape toward fluid port 98.

In one embodiment the mesh 100 has a thickness between 1/4 and 3/16 inches. The embodiment having the dam and drain arrangement is particularly useful to surgeons performing Trendelenburg procedures where the end of the table where the patient's head is placed is lower than the end where the buttocks are supported.

In one embodiment shown in FIG. 7 pocket 84 has an inner portion 104, which is enclosed within it. Inner portion 104 has a plurality of apertures 106 in the walls thereof to facilitate passage of fluid through it while retaining tissue fragments. A further port 108 allows collection with a fluid suction apparatus or can be capped to retain collect fluid in the pocket until it is desired to remove it.

The fluid control island 20 and all of the alternative embodiments and all of their equivalents disclosed herein can comprise a component of a system for collecting fluids coming from a patient during surgery to allow determination of the fluid balance of patients, particularly with respect to distension media, but applicable to other fluids, as well. This island can also be used independently to remove fluids from orthopedic surgeries on smaller joints such as the hand, arm and shoulder.

The fluid collection island 20 system is also adapted for birthing and can be used to make clean up quicker and easier after most surgical and endoscopic diagnostic procedures. In applications such as birthing where quantification of fluid volume may not be required, the base 22 may be made deeper so that a larger volume of fluid can be retained and a lower evacuation rate can be adequate to remove fluid flow rate surges without exceeding the volumetric capacity of the apparatus. Fluid flow surges, inherent in some procedures, can also result from instrument flushing, cleanup, connection failure, and other causes. By routing all fluid flow to the fluid collecting island 20 and quantitatively recovering those fluids, those conditions and events do not become sources of uncertainty.

Changes and modifications in the specifically described embodiments can be carried out without departing from the scope of the invention, which is intended to be, limited only by the scope of the appended claims.

The invention claimed is:

1. A fluid collection island, comprising:
   a central region;
   a further region surrounding the central region and having a peripheral edge for engaging a tray supporting surface, at least a portion of an upper surface of the further region sloping gently upwardly from a peripheral edge thereof to a summit to define a boundary with the central region, at least a portion of an outer edge of the surface of the central region sloping sharply upwardly to the boundary to define a peripheral wall for a fluid collecting vessel the central region having a floor portion which slopes inwardly and upwardly away from an outer edge of the central region to a centrally disposed apex region.

2. The island of claim 1 wherein the further region has at least one indentation formed therein, at least one indentation having a floor portion substantially parallel to the tray supporting surface and steeply angled wall portions from a floor to the upper surface of the further region, at least one of the indentations substantially perpendicularly intersecting the peripheral edge of the further region.

3. The island of claim 2 wherein the at least one indentation has a segment of one of the wall portions closely adjacent and substantially parallel to the peripheral wall of the fluid collecting vessel.

4. The island of claim 3 wherein a fluid removal fitting is clamped to the segment and with a fluid collecting end thereof disposed in the fluid collecting vessel adjacent the peripheral wall of the fluid collecting vessel and a coupling end thereof adapted for connection to a suction line.

5. The island of claim 3 wherein the surface of the further region has a peripheral groove inserted therein for receiving a fluid suction line connected to fluid removal fitting.

6. The island of claim 4 also comprising a resilient cover affixed to the surface of the further region for covering at least a portion of a further groove in the further region and that portion of the suction line inserted therein.

7. The island of claim 1 wherein the surface of the floor portion of the central region has at least one groove in the surface thereof for channeling fluid received on the floor portion away from the apex region to the region adjacent a peripheral wall of the central portion.

8. The island of claim 7 wherein a splash pad substantially fills the fluid collecting vessel in the central region of the island and the longitudinal cross-section of at least one groove for channeling fluid from the apex region to the region adjacent the peripheral wall of the central portion has a radius of curvature which is sufficient to leave a space between the between a bottom surface of the splash pad and the groove to allow free flow of fluid received in the channel after passing through the splash pad.

9. The island of claim 7, wherein the surface of a floor of the central region also includes a peripheral groove adjacent the peripheral wall which receives fluid from the at least one groove.

10. The island of claim 9 wherein the peripheral groove in the floor of the central region drains into at least one collection well positioned below the remainder of the floor of the central region.

11. A fluid channeling and collecting surgical drape, comprising:
   a first sheet having a first portion to place between a patient and a support surface and a second portion to extend downwardly from the support surface;
   at least one resilient strip affixed to a bottom surface of the first portion of the sheet, the resilient strip positioned adjacent the periphery of the first portion of the sheet to form a dam impeding flowage of fluid received on the first portion of the sheet; and a second sheet positioned beneath the first sheet and the resilient strip to form a fluid reservoir and wherein the first sheet has at least one perforation therein adjacent the dam to permit fluid flowing toward the dam to enter the reservoir.

12. The drape of claim 11 wherein at least one evacuation port is provided to allow removal of fluid from the reservoir.

13. The drape of claim 12 wherein a sheet of support mesh is sandwiched between the first and second sheets in the reservoir to support the patient and allow fluid to move about freely in the reservoir.

14. The drape of claim 12 wherein a sheet of support mesh is sandwiched between the first and second sheets in the reservoir to support the patient and allow fluid to move about freely in the reservoir to the evacuation port.

15. The drape of claim 11 wherein a debris pouch attached to the second portion of the sheet to receive tissue and fluid flowing away from the first portion of the first sheet.

16. The drape of claim 15 wherein the debris pouch has an evacuation port for allowing removal of fluid collected therein.

17. The drape of claim 15 wherein the debris pouch has a screen contained therein for receiving fluid and tissue flowing along the drape and retaining the tissue fragments while allowing the liquid to continue to flow into the pouch.

18. A fluid channeling and collecting surgical drape, comprising:
   a first sheet having a first portion to place between a patient and a support surface and a second portion to extend downwardly from the support surface; and
   at least one resilient strip affixed to a bottom surface of the first portion of the sheet, the resilient strip positioned adjacent the periphery of the first portion of the sheet to form a dam impeding flowage of fluid received on the first portion of the sheet wherein the resilient strip is hinged to permit the drape to be unfolded from a compact folded initial configuration to an extended configuration for fluid removal use.

19. The drape of claim 18 wherein the resilient strip has cuts across it to facilitate folding the drape.

20. The drape of claim 19 wherein the cuts in the resilient strip are angled to remove material to facilitate hinging of the resilient strip.

21. A fluid collecting system comprising:
   a fluid collecting island having a central region and a further region surrounding the central region and having a peripheral edge for engaging a tray supporting surface, at least a portion of an upper surface of the further region sloping gently upwardly from a peripheral edge thereof to a summit to define a boundary with the central region, at least a portion of an outer edge of the surface of the central region sloping sharply upwardly to the boundary to define a peripheral wall for a fluid collecting vessel, and having a splash pad positioned to substantially fill the fluid collecting vessel; and
   a drape having its proximate end affixed to the fluid collecting island, the drape having a having a first portion to place between a patient and a support surface and a second portion to extend downwardly from the support surface and at least one resilient strip affixed to a bottom surface of the first portion of the sheet, the resilient strip positioned adjacent the periphery of the first portion of the sheet to form a dam impeding flowage of fluid received on the first portion of the sheet.

22. A kit for assembling a fluid control system comprising, in combination:
   a fluid collecting island having a central region and a further region surrounding the central region and having a peripheral edge for engaging a tray supporting surface, at least a portion of an upper surface of the further region sloping gently upwardly from a peripheral edge thereof to a summit to define a boundary with the central region, at least a portion of an outer edge of the surface of the central region sloping sharply upwardly to the boundary to define a peripheral wall for a fluid collecting vessel;
   a foot pad sized to substantially fill the fluid collecting vessel of the island;
   a fluid removal fitting to be mounted for removing fluid from the fluid collecting vessel of the island; and
   a drape having its proximate end affixed to the fluid collecting island, the drape having a having a first portion to place between a patient and a support surface and a second portion to extend downwardly from the support surface and at least one resilient strip affixed to a bottom surface of the first portion of the sheet, the resilient strip positioned adjacent the periphery of the first portion of the sheet to form a dam impeding flowage of fluid received on the first portion of the sheet, the second portion having a pre-applied adhesive strip for attaching the second portion of the sheet to the peripheral wall of the vessel of the island.

23. A disposable surgical and diagnostic fluid control island placeable on an operating room floor for selectably collecting, retaining and draining fluids received from patients during surgery comprising:
   a generally broad, shallow, impermeable vessel-forming base having
      a peripherally floor-contacting, undersurface portion and an upper surface portion with a raised center,
      a multiplicity of sloping channels extending downward from the raised center toward a lower peripheral channel at the base of a generally vertical peripheral wall disposed between a fluid-contacting central portion and a distal peripheral skirt,
      a generally beveled upper skirt surface extending between the top of the generally vertical peripheral wall and a distal base edge proximate the floor,
   a generally non-absorbent splash pad disposed within the fluid-contacting central portion and supported by ribs above the sloping channels and extending proximal to the raised peripheral wall, and
   means for connecting fluid-removing suction tubing proximate the lower peripheral channel.

24. The disposable surgical and diagnostic fluid control island defined in claim 23 wherein an elongated drape lower end is affixed to the base proximate the peripheral wall and an elongated drape upper end may be disposed upon an operating table for fluid communication between a patient and the base.

25. The disposable surgical and diagnostic fluid control island defined in claim 24 wherein the means for connecting suction tubing is further comprised of a tubular portion and a catch portion, the catch portion being adapted for being affixed proximate the top of the peripheral wall.

26. The disposable surgical and diagnostic fluid control island defined in claim 25 being further comprised of a generally peripheral suction tubing guide channel set into the upper skirt surface interposed between the peripheral wall and the distal edge.

27. The disposable surgical and diagnostic fluid control island defined in claim 26 wherein the suction tubing guide channel is further comprised of tubing retaining nibs.

28. The disposable surgical and diagnostic fluid control island defined in claim 26 being further comprised of a generally planar tubing retainer member resiliently disposed over the suction tubing guide channel.

29. The disposable surgical and diagnostic fluid control island defined in claim 24 being further comprised of a generally peripheral suction tubing guide channel set into the upper skirt surface interposed between the peripheral wall and the distal edge.

30. The disposable surgical and diagnostic fluid control island defined in claim 29 being further comprised of a generally planar tubing retainer member resiliently disposed over the suction tubing guide channel.

31. The disposable surgical and diagnostic fluid control island defined in claim 30 being further comprised of drape-raising resilient members set into the drape upper end.

32. A method for selectably collecting, retaining and draining fluids received from patients during surgery in a disposable surgical and diagnostic fluid control island placeable on an operating room floor comprising the steps of:
   a) placing onto an operating room floor a generally broad, shallow, impermeable vessel-forming base having
      i) a generally horizontal, peripherally floor-contacting, undersurface portion,
      ii) an upper surface portion having a raised center having sloping channels extending downwardly from the center toward a lower peripheral channel at the base of a generally vertical peripheral wall disposed between a fluid-contacting central portion and a radially outwardly disposed skirt,
      iii) a generally beveled upper skirt surface extending between the top of the generally vertical peripheral wall and a distal base edge proximate the floor,
   b) attaching a generally non-absorbent splash pad disposed within the fluid-contacting central portion of the base and supporting the splash pad above the sloping fluid conducting channels that extend proximal to the raised peripheral wall, and
   c) connecting fluid-removing suction tubing to the base proximate the lower peripheral channel.

33. The method of claim 32 further comprising the steps of affixing an elongated drape lower end to the base proximate the peripheral wall and positioning an elongated drape upper end upon an operating table proximate a patient for fluid communication between the patient and the base fluid-contacting central portion.

34. The method of claim 32 further comprising the step of fitting resilient fluid dispersal blocking members between the patient contacting surface of the drape and the operating table.

35. The method of claim 34 further comprising the step of forming a peripheral suction tubing guide channel.

36. The method of claim 35 further comprising the step of affixing a resiliently displaceable tubing retainer member over the suction tubing guide channel.

37. A method of making a disposable surgical and diagnostic fluid control island placeable on an operating room floor for selectably collecting, retaining and draining fluids received from patients during surgery comprising the steps of:
   a) forming a generally broad, shallow, impermeable vessel-forming base having
      i) a generally horizontal, peripherally floor-contacting, undersurface portion,
      ii) an upper surface portion with a raised center having sloping channels that extend from the raised center downwardly toward a lower peripheral channel at the base of a generally vertical peripheral wall disposed between a fluid-contacting central portion and a peripheral skirt,
      iii) a generally beveled upper skirt surface extending between the top of the generally vertical peripheral wall and a distal base edge proximate the floor,
   b) affixing to the base raised center a generally non-absorbent splash pad disposed within the fluid-contacting central portion and supporting the splash pad on ribs disposed above the radial sloping channels and extending proximal to the raised peripheral wall, and
   c) connecting fluid-removing suction tubing proximate the lower peripheral channel.

38. The method of claim 37 further comprising the steps of affixing a lower end of an elongated drape to the base proximate the peripheral wall and disposing an elongated drape upper end upon an operating table for fluid communication between a patient and the base.

39. The method of claim 37 further comprising the step of fitting resilient fluid dispersal blocking members between the patient contacting surface of the drape and the operating table.

40. The method of claim 39 further comprising the steps of connecting suction tubing to the base using a connector having a tubular portion and a catch portion, the catch portion being adapted for being affixed proximate the top of the peripheral wall.

41. The method of claim 39 further comprising the step of forming a peripheral suction tubing guide channel.

42. The method of claim 41 further comprising the step of affixing a resiliently displaceable tubing retainer member over the suction tubing guide channel.

* * * * *

UNITED STATES PATENT AND TRADEMARK OFFICE
CERTIFICATE OF CORRECTION

PATENT NO. : 7,086,409 B2  Page 1 of 1
APPLICATION NO. : 10/892534
DATED : August 8, 2006
INVENTOR(S) : Robinson It is certified that error appears in the above-identified patent and that said Letters Patent is hereby corrected as shown below:

In column 10, line 1, In Claim 1, after "vessel" insert -- ; --.

In column 10, line 24, In Claim 5, after "to" insert -- a --.

In column 11, line 51, In Claim 21, after "having a" delete "having a". (second occurrence)

In column 12, line 10, In Claim 22, after "having a" delete "having a". (second occurrence)

Signed and Sealed this

Fifth Day of December, 2006

JON W. DUDAS
*Director of the United States Patent and Trademark Office*